(12) United States Patent
Balti et al.

(10) Patent No.: US 10,409,226 B2
(45) Date of Patent: Sep. 10, 2019

(54) WEARABLE DEVICE WITH AIR QUALITY SENSOR

(71) Applicants: Haikel Balti, Vitry sur Seine (FR); Charlotte Leger, Montrouge (FR); Frederic Techer, Coulommiers (FR); Nadine Buard, Meudon (FR); Marc Besnard, Paris (FR)

(72) Inventors: Haikel Balti, Vitry sur Seine (FR); Charlotte Leger, Montrouge (FR); Frederic Techer, Coulommiers (FR); Nadine Buard, Meudon (FR); Marc Besnard, Paris (FR)

(73) Assignee: WITHINGS, Issy les Moulineaux (FR)

( * ) Notice: Subject to any disclaimer, the term of this patent is extended or adjusted under 35 U.S.C. 154(b) by 0 days.

(21) Appl. No.: 15/170,479

(22) Filed: Jun. 1, 2016

(65) Prior Publication Data

US 2017/0351221 A1    Dec. 7, 2017

(51) Int. Cl.
*G04B 47/06* (2006.01)
*G01N 33/00* (2006.01)
*G04G 21/02* (2010.01)

(52) U.S. Cl.
CPC ......... *G04B 47/06* (2013.01); *G01N 33/0037* (2013.01); *G01N 33/0039* (2013.01);
(Continued)

(58) Field of Classification Search
CPC ........ G04B 37/08; G04B 47/06; G04G 17/08; G04G 21/00; G04G 21/02; G01N 33/0037;
(Continued)

(56) References Cited

U.S. PATENT DOCUMENTS

| 4,851,088 A | * | 7/1989 | Chandrasekhar .. | G01N 27/4045 204/412 |
| 5,908,546 A | * | 6/1999 | Rollick .............. | G01N 27/4045 204/412 |

(Continued)

FOREIGN PATENT DOCUMENTS

| CN | 204 009 395 U | 12/2014 |
| CN | 204 086 834 U | 1/2015 |

(Continued)

OTHER PUBLICATIONS 5 best water resistant smartphone for summer 2016—phonearean.com—May 12, 2016.*

(Continued)

*Primary Examiner* — Sean P Kayes
(74) *Attorney, Agent, or Firm* — Miller, Matthias & Hull LLP

(57) ABSTRACT

A wearable device with an air quality sensor, the wearable device, comprising a housing enclosing an electronic board, a display arrangement, a battery, the housing lodging a cavity with an internal area, the cavity containing an air quality sensor in the internal area, the cavity being delimited by a cavity wall and by a membrane, the membrane having an inner wall oriented toward the cavity internal area and an outer wall opposed to the inner wall, the internal area of the cavity being in fluid communication with the ambient air through the membrane, the membrane being permeable to air and substantially not permeable to water.

17 Claims, 5 Drawing Sheets

(52) U.S. Cl.
CPC ......... *G01N 33/0042* (2013.01); *G04G 21/02* (2013.01); *Y02A 50/245* (2018.01); *Y02A 50/247* (2018.01)

(58) Field of Classification Search
CPC ........... G01N 33/0039; G01N 33/0042; Y02A 50/247; Y02A 50/245
See application file for complete search history.

(56) References Cited

U.S. PATENT DOCUMENTS

| | | | | |
|---|---|---|---|---|
| 2006/0133213 | A1* | 6/2006 | Robert | G04G 21/02 368/11 |
| 2013/0310710 | A1* | 11/2013 | Eswaran | A61B 5/02411 600/591 |
| 2014/0275854 | A1* | 9/2014 | Venkatraman | A61B 5/721 600/301 |
| 2014/0277624 | A1 | 9/2014 | Pariseau et al. | |
| 2015/0077737 | A1* | 3/2015 | Belinsky | G01N 21/53 356/51 |
| 2015/0226585 | A1* | 8/2015 | Yang | G01D 11/245 73/431 |
| 2015/0238141 | A1 | 8/2015 | Lai | |

FOREIGN PATENT DOCUMENTS

| | | |
|---|---|---|
| KR | 101 598 908 B1 | 3/2016 |
| WO | WO 2015/160830 A1 | 10/2015 |

OTHER PUBLICATIONS

Hydro specsheet—Aug. 2012.*
Hydro Reach—kyoceramobile.com—copy obtained Sep. 19, 2017—Item identified by google search as prior to May 2016.*

* cited by examiner

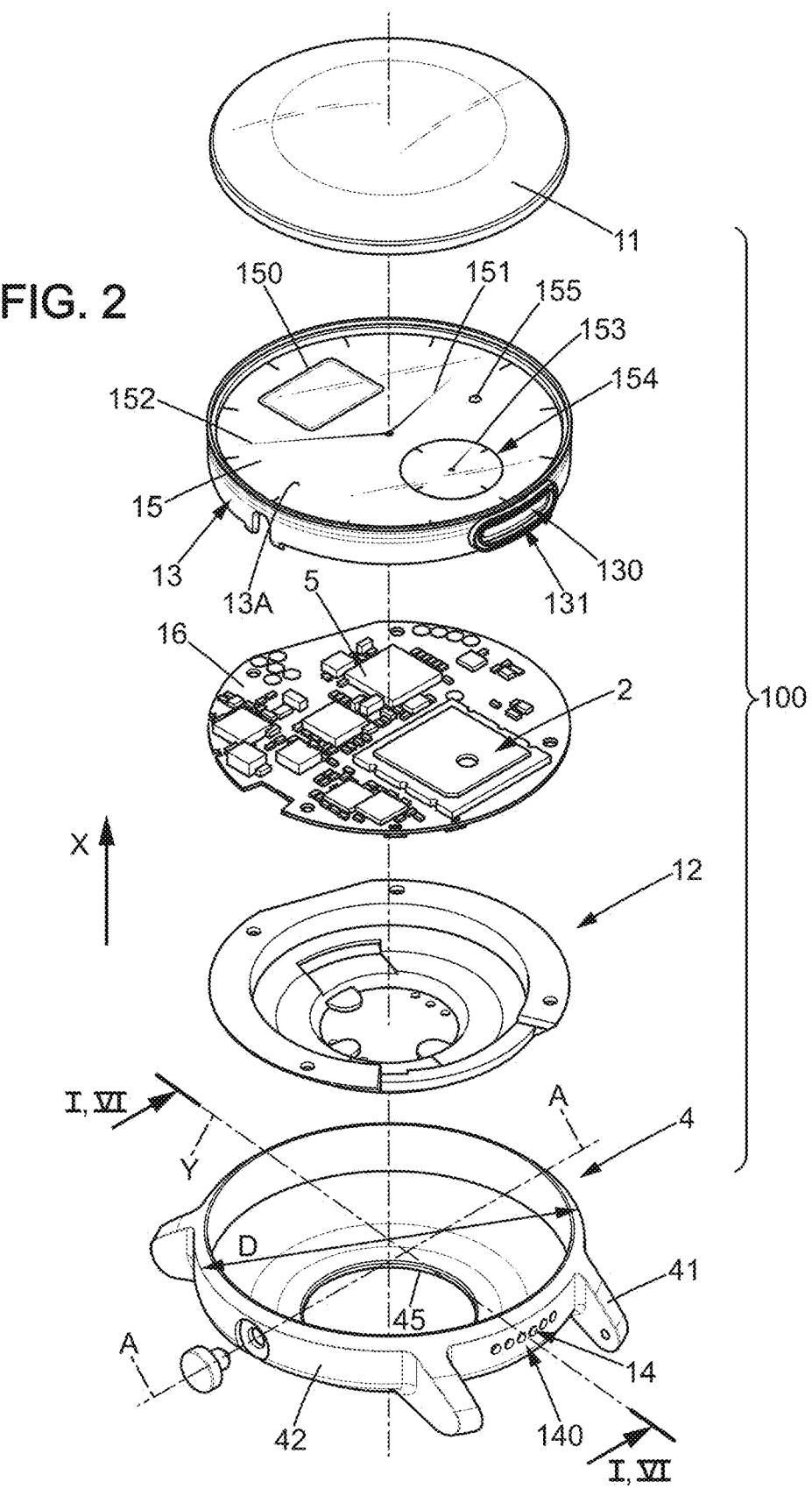

WEARABLE DEVICE WITH AIR QUALITY SENSOR

FIELD OF THE DISCLOSURE

The present invention concerns a wearable device, like a wrist watch or an activity tracker, with an embedded air quality sensor. Here, the term 'air quality sensor' encompasses any sensor able to determine a concentration level of some chemical compound in the air which can have an impact on human health (otherwise called "pollutants"), among them for example $NO_2$, $O_3$, NOx, CO, $SO_2$, and others, without excluding chemical components which can have a long term impact on mankind environment like $CO_2$, $O_3$, etc. . . . .

BACKGROUND OF THE DISCLOSURE

Recently, some have suggest to include an air quality sensor into a device like a wrist watch, as disclosed in documents US2014277624 and US2015238141. However, these attempts to include an air quality sensor into a wrist watch remain rather unrealistic proposals and/or exhibit a rather bulky configuration.

Furthermore, the attempts to embed an air quality into a wrist watch have not taken into account various everyday life environmental conditions to which the wrist watch (or 'wearable device') is submitted. For example, a wrist watch is exposed to water when the user washes or rinses his/her hands. Sometimes the user sweats and the surface of the watch adjacent to the skin may become wet or even dirty on the long run.

Also, a wrist watch is usually exposed to mechanical stress like shocks and free falls, and therefore, all the elements exposed to the outside must be rugged and solid.

Also, a wrist watch must remain in a size compatible with men and women size standards.

Also, many recently marketed multi-function watches or smart watches tend to have an insufficient energy autonomy, requiring frequent recharges or battery replacement(s).

Finally, it is desirable that the basis for air quality evaluation by the sensor should be substantially in real time, and thus the air sample subject to analysis shall be renewed frequently enough.

Therefore, there remains a need to provide a watch or a wearable device with an embedded air quality, robust and providing reliable measurements for the air quality, whatever the condition of use regarding the watch.

SUMMARY OF THE DISCLOSURE

According to one aspect of the present invention, it is disclosed a wearable device with an air quality sensor (2), the wearable device comprising a housing (100) enclosing an electronic board (16), a display arrangement (15), a battery (6), the housing lodging a cavity (1) with an internal area, the cavity containing an air quality sensor in the internal area, the cavity being delimited by a cavity wall and by a membrane (3), the membrane having an inner wall (30) oriented toward the cavity internal area and an outer wall (31) opposed to the inner wall, the internal area of the cavity being in fluid communication with the ambient air through the membrane, wherein the membrane being permeable to air and substantially not permeable to water.

It is to be noted that the wearable device is to be broadly construed. The wearable device can typically be a watch, a wrist watch or an activity tracker, without excluding other types of personal wearable devices (glasses, necklace, ring, etc. . . . ).

Thanks to these dispositions, the air quality sensor is protected inside the housing of the wearable device against damages. Namely, the wearable device can withstand shocks or falls without negative impact on performance. Particularly, the air quality sensor is perfectly protected inside the wearable device, whereas, at the same time, the sensor is able to sense various concentration of chemical compounds present in the air outside the wearable device, thanks to the fluid communication channel through the membrane which is permeable to air.

Furthermore, the user can for example immerse briefly his wrist wearing the watch (or generally wearable device) in water without damaging the sensor since the membrane forms a barrier against ingress of water.

Moreover, the arrangement of the sensor in the cavity of the housing enables to perform a reliable measurement of pollutants.

The wearable device can be used on one hand to detect pollutants in the general environment of the user, and on the other hand to detect some particular chemical species present in the breath of the user when the user exhales or blows toward the wearable device.

The term "display arrangement" should be here construed broadly. According to one embodiment, the display arrangement may comprise analog type indicators, namely with physical stick-like hands forming analog time display indicators and additionally an auxiliary hand to display a current amount of physical activity performed by the user wearing the watch. According to another embodiment, the display arrangement may comprise digitalized pixel area, able to display a large variety of items including virtual hands for time indication.

According to still another embodiment the display arrangement may comprise both a digitalized pixel area, and physical stick-like hands forming analog indicators (for time and other data).

In various embodiments of the invention, one may possibly have recourse in addition to one and/or other of the following arrangements.

According to one option, the internal area of the cavity (1) is in fluid communication with the ambient air exclusively through the membrane (3), the cavity being elsewhere tightly isolated from the inside of the housing (100). Thereby, possible polluting gazes that may come from the inside of the watch itself (e.g. from electronic component or battery or coating material) can be advantageously prevented.

According to one option, the housing (100) is formed by a main casing (4), a transparent cover (11) and a back cup (12), the main casing comprising at least one through bore (14) located in an perforated area (140) for fluid communication between the internal area of the housing and outside environment, the outer wall of the membrane (31) facing the perforated area. Thereby, the membrane is not exposed directly to the outside environment, the main casing offers mechanical protection together with fluid communication; air passage is enabled across the through bores toward the membrane, and further across the membrane toward the air quality sensor. Air renewable is sufficient for real-time analysis.

According to one option, the air quality sensor (2) is able to sense and determine the concentration of NO2 and O3. Such a dedicated focused sensor advantageously exhibits a small size and a very low electrical consumption.

According to one option, the air quality sensor (2) is able to sense and determine the concentration of CO and/or NO2 and/or SO2. Thereby, the concentration of most common air pollutants can be determined, and according to a further option reported wirelessly to mobile device of a user.

According to one option, the air quality sensor (2) includes an amperometric sensor with a power consumption below 5 micro-amps. Thereby, the lifetime of the battery can be substantially improved if compared with some other wearable devices including gas sensor(s).

According to one option, the air quality sensor (2) includes an amperometric sensor with a volume less than 0.2 cm$^3$. Thereby, such sensor can be integrated in a standard watch volume, even in a standard women watch volume.

According to one option, when the wearable device is a watch, the cavity wall is delimited by a dial plate (13) and by the air quality sensor (2), the dial plate (13) defining a top portion and a side portion of the cavity wall, a bottom portion of the cavity wall being formed by the air quality sensor (2), the interface between the sensor (2) and the dial plate (13) being locally sealed, the cavity wall comprising on the side portion an opening (130) closed off by the membrane (3). Thereby, the dial plate provides an integrated solution to lodge the air quality sensor and to provide an air cavity. The bill of material and manufacturing process are thereby optimized.

According to one option, the interface between the sensor (2) and the dial plate (13) is sealed using at least one gasket (8).

Elastomeric gasket in a groove is a reliable solution to provide fluid tightness.

According to one option, there is provided a shoulder (131) formed in the dial plate (13) around the opening (130) from a surface of the dial plate opposed to the cavity wall, the membrane (3) being tightly received against the shoulder. It is therefore easy to glue or solder by ultrasonic vibrations the membrane on the shoulder so that it closes tightly the cavity and the border of the opening.

According to one option, there is provided an inner space (132) located between the membrane (3) and the perforated area (140), the inner space (132) being insulated from the inside of the housing (100) using a gasket (82) inserted between the housing (100) and the dial plate (13) close to the opening (130).

This allows to handle possible manufacturing play entailed by deviations of dimensions in an industrial process.

According to one option, the display arrangement may comprise a plurality of physical stick-like hands forming analog indicators and at least a digital display area. This kind of mixed solution advantageously enhances comfort and readability from the user standpoint.

According to one option, each through bore has typically a dimension comprised in the range 0.05 and 1.5 mm; a preferred range for the bore diameter is [0.5 mm, 1.5 mm]. Although the through bores can have any dimension, this particular range avoids a water meniscus which could obstruct the bore after exposition to water.

According to one option, the electronic board (16) comprises a hole (160), the size of the hole being adapted for receiving the air quality sensor through said hole, the sensor emerging from both sides of the electronic board.

We obtain therefrom an advantageous integration of the air sensor, a compact piling up of components, enabling a thin package and giving a low thickness of the watch.

The display arrangement may further comprise a multi-color indicator Led, whose color is controlled by the electronic board according to the sensed level of air pollutants in the sampled air; whereby the user can have a very simple feedback of the current air quality around him/her.

The watch may further comprise a vibrator, controlled by the electronic board which is configured to activate the vibrator in case the sensed level of pollutants exceeds a predefined threshold; whereby the user can be warned at any time, even though he/she does not look at his/her watch.

According to one option, the air quality sensor (2) may be able to determine the concentration of NO, and, whenever the user exhales towards the wearable device, the wearable device may be used to detect asthma, emphysema or similar lung disease from the breath of the user.

BRIEF DESCRIPTION OF THE DRAWINGS

Other features and advantages of the invention appear from the following detailed description of one of its embodiments, given by way of non-limiting example, and with reference to the accompanying drawings, in which:

FIG. 2 shows an exploded view of the wristwatch of FIG. 1, FIGS. 3a and 3b show perspective views of the dial plate, from the bottom site and respectively from two different viewpoints.

DETAILED DESCRIPTION OF THE DISCLOSURE

In the figures, the same references denote identical or similar elements.

Figure 1:
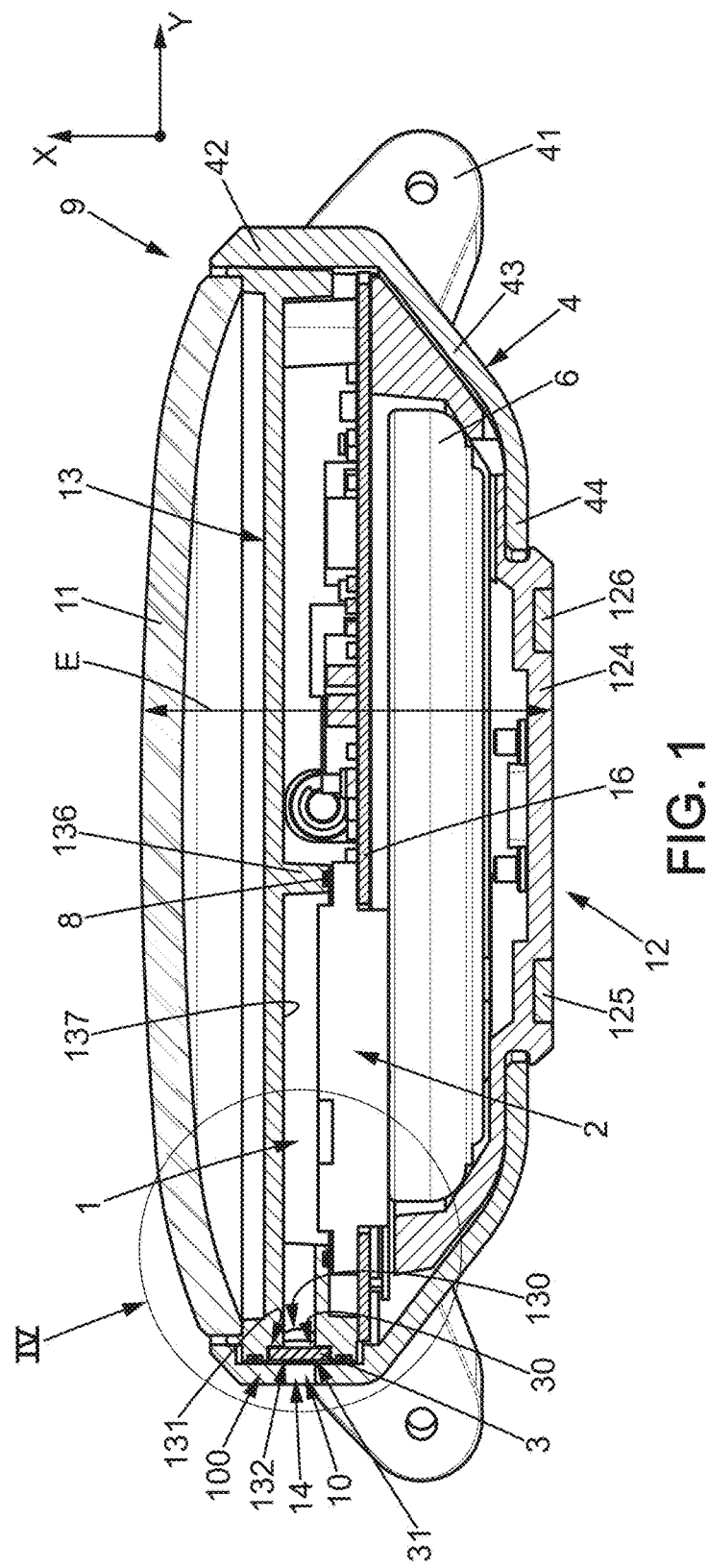
FIG. 1 shows an elevation cross section of a wristwatch according to the present disclosure.

As illustrated on FIGS. 1 and 2, one exemplary embodiment of the present disclosure relates to a wrist watch 9. The wrist watch in question exhibits a standard size suitable for both men and women. An example of such a device is a watch name "Activité™" from the present applicant "Withings™". The body of the watch has preferably an external diameter D of 42 mm or less; the thickness E of the body is 14 mm or less. Preferably, the thickness E may be 12.5 mm or 12 mm.

From the body, there are provided projections 41 for attachment to a wristband 19 as known per se, thus not described in detail here.

The wrist watch 9 illustrated here is a digital watch, namely all the indications given on the front face of the watch are given by a high definition dot matrix display, of LED or OLED technology, which is referred to herein as display arrangement 15.

Virtually, almost any object can be displayed using this type of display, pictograms, numbers, digitalized areas 150. Also, virtual hands 151,152 (for hours and minutes display) can be displayed using such high definition display; there can be provided an auxiliary indicator 153 as well.

Alternately, the present invention can be applied to an analog type watch, that-is-to-say a watch where the time is indicated through a dial and solid stick-like hands (one for hours, one for minutes, and optionally one for seconds) driven by stepper motors and gear trains as known per se.

Alternately, the present invention can be used in a hybrid watch, having both solid stick-like hands and digitalized display area.

In a preferred illustrated embodiment, the body of the watch is substantially round; but in other embodiments, the body of the watch can be substantially square or rectangle.

As illustrated, particularly visible on FIG. 2, the exemplified watch comprises, from bottom to top:
- a main casing 4,
- a back cup 12,
- a battery 6,
- a printed circuit board 16 and a sensory device 2,
- a dial plate 13, otherwise called "dial support",
- a top cover 11, which is transparent.

The vertical direction denoted X is defined as the direction transverse to the plane of the watch dial. The thickness of the watch is defined along this vertical direction X.

Further, there is also defined a longitudinal direction denoted Y, perpendicular to X and which corresponds to the main direction of extension of the wristband 19 from the watch. Further, a third direction, perpendicular to the other ones, is named "transversal" and denoted A. The plane A,Y is referred to as a watch plane.

According to the present disclosure, there is defined a housing 100 of the wrist watch 9 which includes the main casing 4, the back cup 12 and the top cover 11; the housing can also be called "enclosure" since it encloses and protects all the internal components and elements contained in the watch.

As illustrated on FIGS. 1 and 2, the main casing 4 comprises a cylindrical portion 42 having a vertical axis; the cylindrical portion 42 is prolonged downwards by a tapered frustoconical portion denoted 43; the tapered portion is further prolonged downward by a flat ring portion 44. The flat ring portion 44 is shaped as a disc with X axis, and comprises a large central opening 45.

The main casing 4 is preferably manufactured in stainless steel; alternatively light alloy or high-performance plastics like ABS, or other robust plastic material, can also be considered.

The back cup 12 is formed like a cup with a bottom section inserted in the above mentioned central opening of the main casing. The bottom section is prolonged upwards by a tapered portion adjacent internally to the tapered frustoconical portion of the main casing.

The back cup 12 is manufactured from a plastic rigid material, for example ABS or polycarbonate.

Advantageously, the above-mentioned sensory device 2 is an air quality sensor 2 which is enclosed in the housing.

The air quality sensor 2 is used to determine the rate of pollutants in the air prevailing at the vicinity of the watch. It should be noted that the samples collected at the watch are not substantially different from the air that the user/wearer of the watch is breathing.

More precisely, the air quality sensor 2 is enclosed in a cavity 1 provided in the housing 100.

The cavity 1 is delimited by a cavity wall and by a membrane 3, which is advantageously porous. The cavity 1 is in fluid communication with the ambient air through the membrane 3 as this will be described in detail later.

In use, the air enters the housing of the watch 100 and passes across the membrane 3. The pollution rate is measured by the sensor 2 in the internal area of the cavity 1.

According to one first possibility, the air quality sensor 2 can be a sensor mainly reactive to NO2 (Nitrogen Dioxide). According to another possibility, the air quality sensor 2 can be a sensor mainly reactive to NO (Nitrogen Oxide).

According to another possibility, the air quality sensor 2 can be a sensor mainly reactive to SO2 (Sulfur Dioxide). According to another possibility, the air quality sensor 2 can be a sensor mainly reactive to CO (Carbon Monoxide).

According to another possibility, the air quality sensor 2 can be a sensor mainly reactive to H2S (Hydrogen Sulfide).

According to other possibilities, the air quality sensor 2 can be a sensor mainly reactive to CO2 (Carbon Dioxide) or a sensor mainly reactive to ozone (O3) or a sensor mainly reactive to chlorine or a sensor mainly reactive to benzene, or a sensor mainly reactive to methane.

According to another possibility, the air quality sensor 2 can be a sensor reactive to two or more of the above mentioned chemical compounds.

According to a preferred embodiment, the air quality sensor 2 is reactive both to NO2 and O3, with a higher gas selectivity than known general-purpose pollutants sensors, like for example the so-called VOC sensors.

The physics of the sensor(s) relies on electrochemical reactive process, with a chemical layer combined with a transducer like typically an amperometric sensor.

A working electrode (or catalyst) promotes a chemical reaction when in contact with the gas, which takes place with regard to a second electrode (common=counter electrode).

For example, respective chemical reaction for CO and NO2 are:

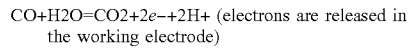
$CO+H_2O=CO_2+2e-+2H+$ (electrons are released in the working electrode)

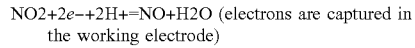
$NO_2+2e-+2H+=NO+H_2O$ (electrons are captured in the working electrode)

Chemical interaction velocity follows the Arhenius law with a certain activation energy E which depends on many parameters: $Kc$ (speed)$=A \exp(-E/RT)$ The kinetics of a given chemical reaction makes a corresponding sensor responding immediately to a certain gas and very slowly to another one.

A bias reference voltage is set to the working electrode which results in a current flowing from/to the working to the ground electrode, the current depending on the kinetics of the considered chemical reaction.

Electrolyte is provided between the two electrodes to transport the H+ ion from one electrode to the other electrode.

According to one exemplary choice, one can select product reference 3SP_NO2_20 from SPEC Sensors, LLC, of Newark, Calif. Advantageously, thanks to its fuel-cell like technology, the air quality sensor 2 exhibits a very low electrical consumption, namely an average consumption when powered less than 5 microAmps, preferably less than 2 microAmps.

If we consider additionally the polarisation current from the main PCB, the total amount of current used for the sensor is preferably less than 10 microAmps Therefore, with a conventional lithium battery 6 for a watch, for example of the type CR2025 or CR2032 ("button cell"), the lifetime of the battery can be advantageously more than one year, preferably around 18 months or even two years.

It should be noted that in one embodiment, even though the sensor is permanently supplied, the sampling of sensor signal is made from time to time to lower further the electrical consumption.

It is important to note that more than one sensor can could be arranged in the air cavity, for examples two sensors or more.

Figure 5:
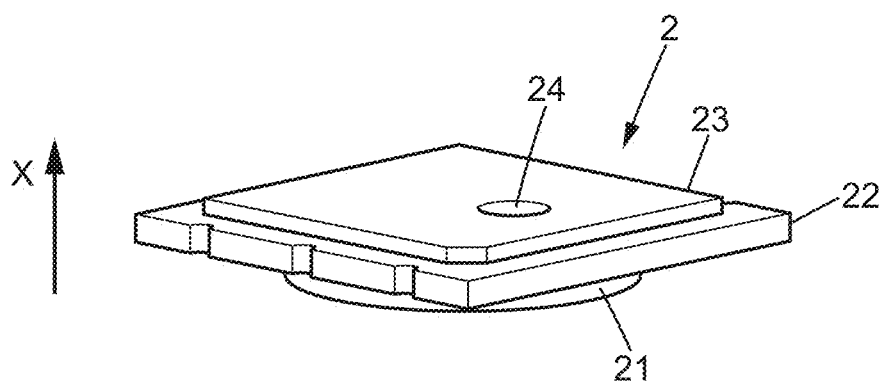
FIG. 5 shows an enlarged view of the air quality sensor.

As shown on FIG. 5, the exemplified air quality sensor 2 is composed of three sections, one above the other along the vertical direction. The lower section denoted 21 is in form of a disc and has a circular periphery. The lower section houses an electrochemical cell comprising a reactant like an electrolyte or a gel.

The lower section is followed upwards by an intermediate section 22, having a rectangular shape. The intermediate section 22 is a ring shaped thin PCB for electrical connection to the main printed circuit board 16 (soldering face-to-face).

A top portion 23 has also rectangular shape, but with smaller dimensions in the shown example. The top portion 23 forms a cover and comprises a recess 24 opened in the surface of the top portion to let the air enter the sensitive part below.

The largest section of the air quality sensor 2 exhibits dimensions in the plane A,Y of the watch, comprised between roughly (5 mm×5 mm) and (15 mm×15 mm), typically around 10 mm×10 mm.

A particular mechatronic integration solution will be explained further.

However, it should be noted that the geometric configuration of the air quality sensor 2 can be slightly different or completely different.

In the shown example, the cavity 1 is delimited by the dial plate 13 and by the air quality sensor 2. The dial plate 13 defines a top portion 137 and a side portion 136 of the cavity wall. A bottom portion of the cavity wall is formed by the air quality sensor 2 itself.

The dial plate 13 is for example formed in polycarbonate. Although, various other plastic materials can be considered for the dial plate.

Figure 3A:
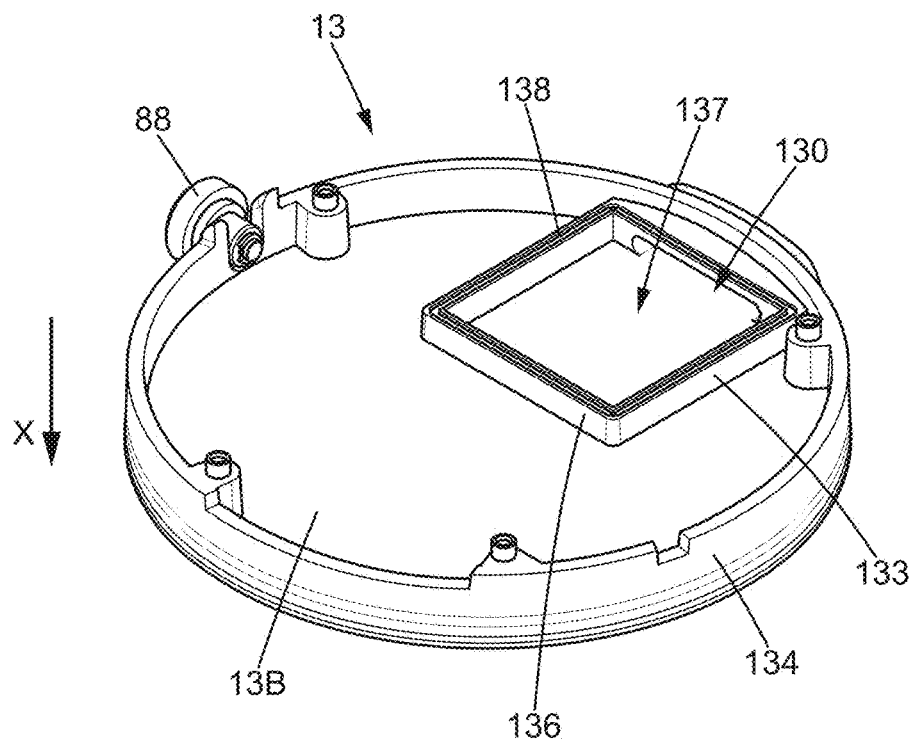
Figure 3B:
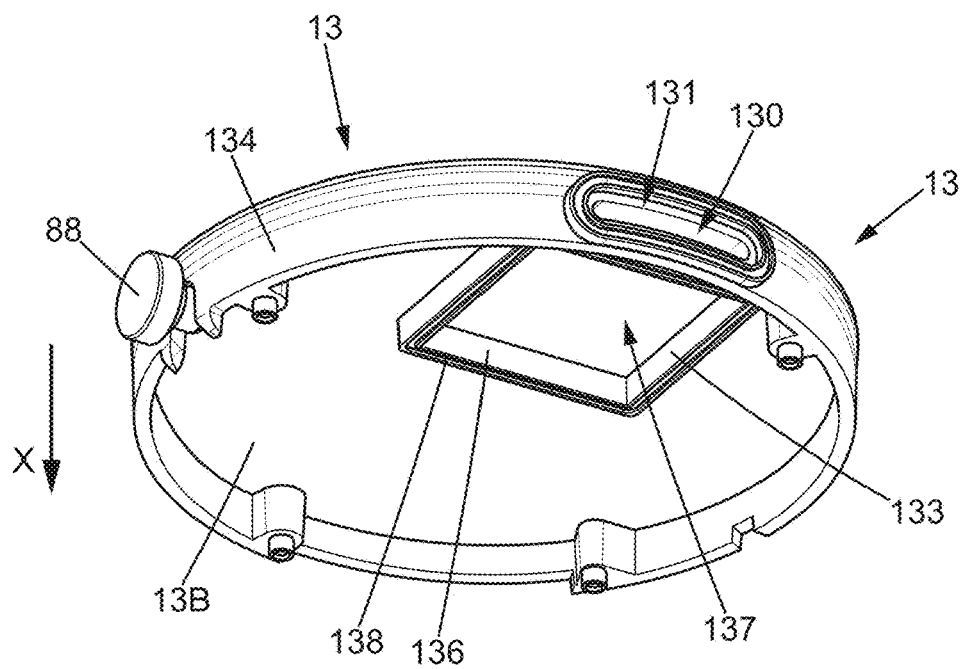

The dial plate 13 is illustrated on FIGS. 3a and 3b in the case of wrist watch housing with a circular shape. The dial plate is a disc with a peripheral rim 134. The disc has a diameter slightly inferior to the internal diameter of the cylindrical portion 42 of the casing 4.

The disc extends in the plane A,Y of the watch with a top side 13A, in which the display arrangement 15 is arranged and a bottom side 13B which faces the printed circuit board 16.

A border 133 extends from the bottom side 13B of the disc downwards in the vertical direction on a length inferior to the height of the peripheral edge from the bottom side of the disc. The border 133 delimits the cavity. The border 133,136 defines in this embodiment typically a rectangular shape.

The cavity has in this embodiment a square shape footprint with side size between 0.5 cm and 1.5 cm.

Alternatively the cavity could have a circular section.

The cavity 1 is closed by the sensor 2 at the bottom side of the cavity 1. More precisely the sensor 2 surface 22a is in contact with the lower end of the border 133, and all along the periphery of the border 133. It is possible to provide a glue or silicon bead to provide a tight junction.

Figure 4:
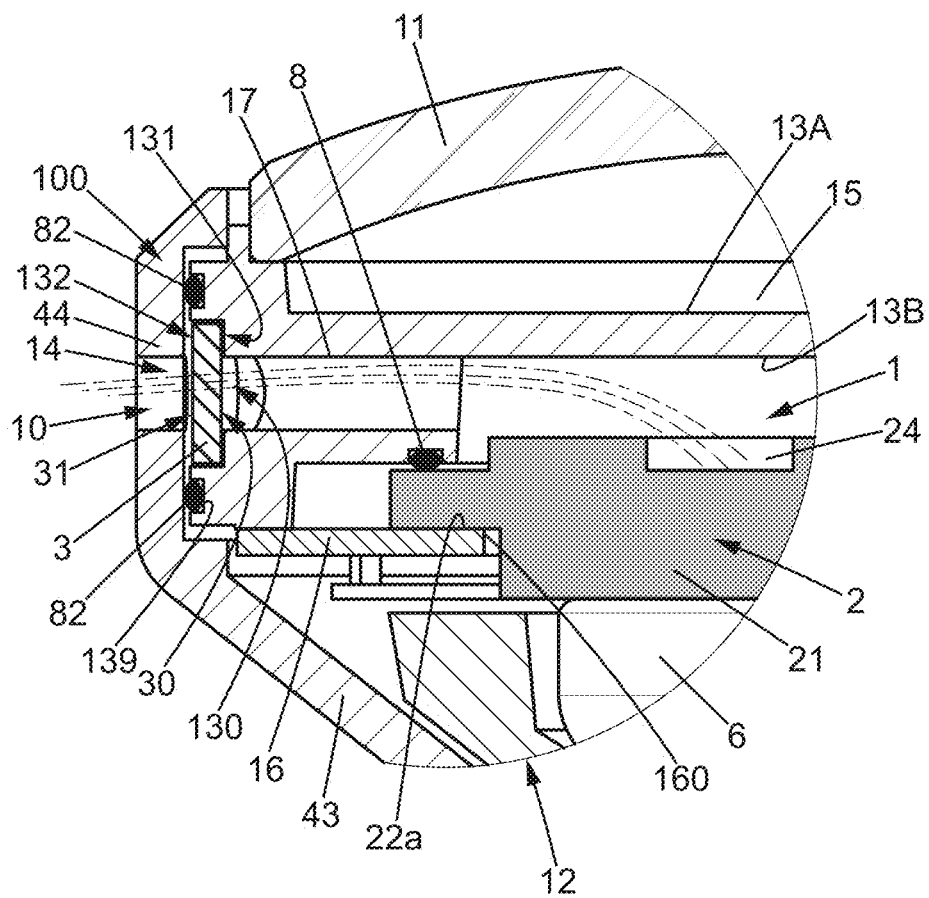
FIG. 4 shows an enlarged sectional view of the membrane area.

Referring to FIGS. 1 and 4, the top section 23 protrudes slightly in the cavity 1. The extremity of the border 133 opposed to the disc comprises in particular a groove 138 along the extremity of the border 133.

A gasket 81 is for example inserted along this junction area between the sensor and the border 133. The gasket 81 has for example a rectangular loop shape matching with the shape of the border of the cavity. The gasket 81 has for example a round cross-section, configured to be inserted in the above mentioned groove 138.

The material of the gasket is chosen to be neutral versus the detection of chemical compounds; among the preferred materials are Viton™, EPDM (ethylene propylene diene monomers), or silicon.

In this embodiment the thickness of the air sensor is typically between 2 mm and 4 mm.

One side of the cavity wall formed by the border 133 is formed nearby the peripheral edge 134 of the disc in a way wherein there is a material continuity and the border 133 and the peripheral edge 134 are locally the same.

A tunnel 17 is open from the internal area of the cavity 1 through the cavity wall locally and then in continuity through the peripheral edge 134, ending in an opening 130 at the surface of the peripheral edge 134. The tunnel 17 connects the internal area of the cavity with the opening 130.

The membrane 3 closes off the cavity wall opening. The membrane 3 is permeable to air and not permeable to water. The membrane 3 comprises a porous material.

The membrane 3 is formed as a thin wall manufactured in synthetic material having a microporous structure. Across the membrane, diffusion is governed by Fick's law.

Various materials are available to achieve water protection while allowing air passage. According to one example, the membrane is made of polytetrafluoroethylene (also called ™Teflon) marketed under ™Gore-Tex membranes. According to another example, the membrane can be made of non-woven high-density polyethylene fibers. Nanopores having a size comprised between 1 μm and 5 μm let the way for air molecules while retaining bubbles of water. The thickness of the membrane 3 is comprised between 50 μm and 500 μm.

The 'Schmerber' index, denoting water non-premeability performance, is at least 5 000; in other words, water cannot passes through the membrane for a pressure difference threshold up to 200 mbar. Preferably this pressure difference threshold is typically 270 mbar.

Likewise, IP rating of the membrane 3 is at least IP64, preferably IP67 or IP68.

Air permeability is at least 70 liter/hour/cm$^2$ at a 70 mbar of pressure difference.

An inner wall 30 of the membrane 3 is oriented toward the cavity internal area and an outer wall 31 is opposed to the inner wall. The internal area of the cavity is in fluid communication with the ambient air through the membrane 3. A shoulder 131 is formed around the opening 130.

In the plane of the peripheral edge 134 from the surface of the peripheral edge toward the cavity internal area. The membrane 3 is in this embodiment inserted in the shoulder 131 in a way wherein the membrane 3 is locally in the plane of the peripheral edge surface.

Alternatively the periphery of the inner wall 30 of the membrane can be welded with ultrasound to the surface of the peripheral edge 134 to close off the cavity.

The opening 130 has in this embodiment an oval shape extending along an axis parallel to the watch plane. So the membrane has a typical oval shape in this embodiment to be placed against the described shoulder.

Alternatively the opening can have a different shape, such as a rectangular shape.

In the illustrated case of a digital watch, any type of object can be displayed as mentioned above.

In the analog type variant, the top side 13A of the dial plate 13 supports in this embodiment the physical pointers 151,152 of the watch for example.

The transparent cover 11 covers the pointers in a way wherein the pointers are visible through the transparent cover 11.

The peripheral edge 134 on the top side of the dial plate 13 comprises a shoulder, as illustrated on FIG. 3c, adapted to insert the peripheral edge of the transparent cover 11 in a watertight way.

The dial plate 13 is enclosed in the housing such as that the disc is parallel to the plane of the watch. In this way wherein the peripheral edge 134 is parallel to the lateral part of the main casing 10 formed by the cylindrical part. The opening 130 faces the lateral part. The membrane 3 is thus parallel to the main casing locally.

The lateral part of the main casing 10 has a vertical extension comprised between 4 mm to 6 mm. The thickness of the watch is roughly the height of the main casing 10 which is in the range of 8 mm to 14 mm.

The main casing 4 is for example obtained from stamping in one piece of stainless steel. The lateral part of the main casing 10 comprises a perforated area 140, wherein through bores 14 are open to connect the internal area of the housing 100 to outside.

The through bores 14 are typically aligned in the perforated area 140, facing the opening 130. There are for example six bores. Each bore 14 has a diameter comprised between 0.05 mm and 1.5 mm and typically of about 1 mm. The through bores 14 are separated by about 1.5 mm.

The internal area of the cavity 1 communicates with outside through the through bores 14 and through the membrane 3. The air enters the housing 100 through the through bores 14 and then enters the cavity 1 through the membrane 3.

The diameter of the through bore 14 is typically given proportionately to size of the cavity 1 to avoid a meniscus effect in particular. The oval opening 130 has a typical extension in a range of 1 cm to 1.5 cm and typically around 1.2 cm. Alternatively the bores could be replaced by a slit.

An inner space 132, illustrated on FIG. 4, is in this embodiment located between the membrane 3 and the opening area 140.

The housing 100 encloses several other items as an electronic board (PCB) 16 with a controller 5, an oscillator, a battery 6 either conventional or rechargeable, etc . . . .

The battery of the watch is typically below the PCB inside the cavity in the bottom part of the housing. Gas is for example possibly emitted by the PCB or by the battery and could disturb the measurement by the sensor 2.

Figure 6:
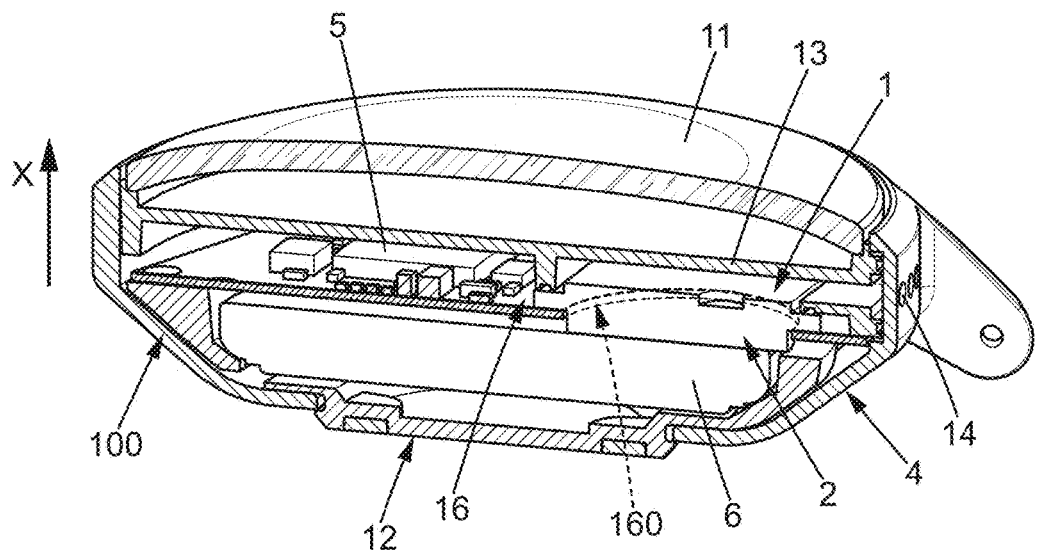
FIG. 6 shows another perspective sectional view of the wristwatch of FIG. 1.

As illustrated on FIG. 6, the PCB is positioned between the battery and the cavity, parallel to the plane of the watch. The PCB comprises a hole 160 in which is inserted the sensor 3. In this configuration, the periphery of the bottom side of the intermediate portion is in contact with the PCB surface. The sensor extends through the PCB in a way wherein the bottom face of the air quality sensor is vertically below the PCB 16.

In this configuration the thickness of the watch housing 100 is minimized with the integration of the air quality sensor through the PCB.

The sensor 2 is connected to a control unit 5 integrated to the PCB 16 which collects and treats air quality data. A diode 155 is for example mounted on the dial plate top face and connected to the control unit. The diode is used to provide for example a light color signal representative of the air quality measured.

Figure 7:
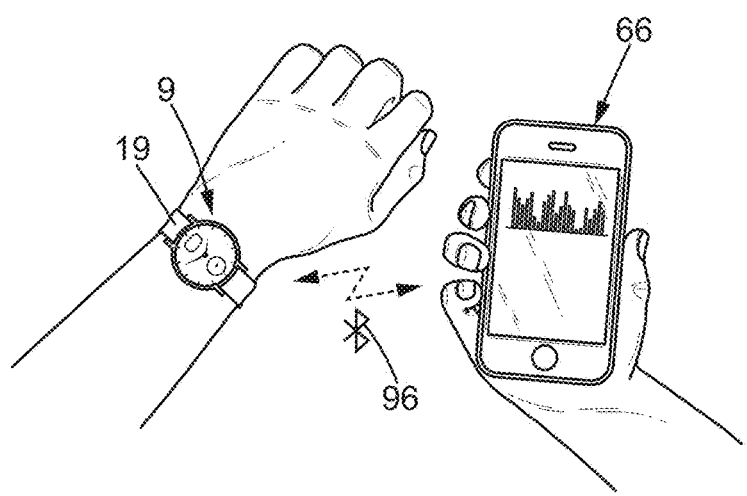
FIG. 7 illustrates a use case with wireless upload of data from the wristwatch of FIG. 1 to a smartphone.

As an alternative or complementarily the watch could be in wireless communication 96 with another device like a smartphone 66, or other devices and the data could be displayed on the screen of the connected device as illustrated on FIG. 7.

Instead of a single led 155, the small bargraph can be used.

Also, the actual sensed values of pollutants can be displayed on the digitalized area 150.

On the smartphone 66, there may be provided histograms of pollutant rate along the present day, along the past three days, along the past week etc. . . .

Additionally, there may be displayed for each pollutant compound, a threshold line showing the predefined alert level, with different colours on histograms whenever the pollutant rate become higher than the threshold(s).

Optionally, there may be provided one or more user actuator 88 otherwise called button; various purposes can be allocated to actuation of such button, as known per se.

In the analog type version, stepper motors and gear trains are arranged preferably on the side of the watch plane opposed to the side where the air quality sensor is placed.

Optionally, the watch is equipped with a photo plethysmograpic (PPG) sensor 125 used to sense the heart rate of the user of the watch. The PPG sensor is arranged on the bottom face of the watch.

Optionally, the watch is equipped with an electrode 124 in contact with the user's skin to form a sensor used for ECG analysis. The electrode for ECG sensing is also arranged on the bottom face of the watch.

Optionally, the watch is equipped with a temperature sensor 126, configurable to measure the skin temperature on the wrist of the user. The skin temperature sensor is also arranged on the bottom face of the watch. There may be provided additionally an ambient temperature sensor.

Optionally, the watch is equipped with a vibrator, which can be used to notify the user with a particular message or a particular alert.

Regarding the predefined thresholds to trigger an alert, the following values can be taken into account.

For $NO_2$, a first threshold value is set at 200 $\mu g/m^3$.

For $NO_2$, a second threshold value is set at 400 $\mu g/m^3$.

Each of the first and second $NO_2$ thresholds are considered in conjunction with a minimum exposure time, for example an exposure duration or a certain number of times when the threshold is exceeded.

For $O_3$, a first threshold value is set at 240 $\mu g/m^3$.

For $O_3$, a second threshold value is set at 300 $\mu g/m^3$.

For $O_3$, a third threshold value is set at 360 $\mu g/m^3$.

Each of the first, second and third $O_3$ thresholds (above-mentioned) are considered in conjunction with a minimum exposure time, for example an exposure duration or a certain number of times when the threshold is exceeded.

Once a particular threshold is exceeded with its associated time condition(s), a local message can be given by vibrations, and/or by a particular color on the indicative Led. Also, one or more messages can be sent immediately to the connected smart phone 66.

As already stated, although the shown embodiment relates to a watch, the configuration of the membrane, the cavity and the air quality sensor can of course be applied to any kind of personal activity tracking device, or any kind of wearable device.

As already stated, the above configuration (for a watch or more generally for a wearable device) with the adequate amperometric gas sensor can also be used advantageously for breath analysis, when the user blows towards the wearable device. Preferably, the result can be faster when the user blows directly towards or into the bores 14.

Breath analysis is a known technique to screen diseases. For example the presence of NO in the breath is a marker for asthma, emphysema or similar lung disease.

The invention claimed is:

1. A wearable device with an air quality sensor, the wearable device comprising a housing enclosing an electronic board, a display arrangement,
the housing lodging a cavity with an internal area,
the cavity containing an air quality sensor in the internal area,
the cavity being delimited by a cavity wall and by a membrane,
the membrane having an inner wall oriented toward the cavity internal area and an outer wall opposed to the inner wall, the internal area of the cavity being in fluid communication with the ambient air through the membrane,
the membrane being permeable to air and substantially not permeable to water,
wherein the cavity wall is delimited by a top portion, a side portion and a bottom portion, the bottom portion of the cavity wall being entirely formed by the air quality sensor, and wherein an interface between the air quality sensor and the side portion is locally sealed, the cavity wall comprising on the side portion an opening closed off by the membrane.

2. The device according to claim 1, wherein the housing is formed by a main casing, a top cover and a back plate,
the main casing comprising at least one through bore located in an opening area for fluid communication between the internal area of the housing and outside, the outer wall of the membrane facing the opening area.

3. The device according to claim 2, wherein each through bores has typically a dimension comprised in the range 0.05 and 1.5 mm.

4. The device according to claim 1, wherein the air quality sensor is able to determine at least one of a concentration of NO2 and O3.

5. The device according to claim 1, wherein the air quality sensor is able to determine at least one of a concentration of NO2 and CO and SO2.

6. The device according to claim 1, wherein the air quality sensor includes an amperometric sensor with a power consumption below 5 micro-amps.

7. The device according to claim 1, wherein the air quality sensor includes an amperometric sensor with a volume less than 0.2 cc.

8. The device according to claim 1, wherein the device is formed as a watch and wherein the cavity wall is delimited by a dial plate and by the air quality sensor, the dial plate defining the top portion and the side portion of the cavity wall.

9. The watch according to claim 8, wherein the interface between the sensor and the dial plate is sealed using at least one gasket.

10. The watch according to claim 8, wherein a shoulder is formed in the dial plate around the opening from a surface of the dial plate opposed to the cavity wall, the membrane being received against the shoulder.

11. The watch according to claim 10 wherein an inner space is located between the membrane and a perforated area, the inner space being insulated from the inside of the housing using a gasket inserted between the housing and the dial plate close to the opening.

12. The watch according to claim 1, wherein the display arrangement comprises a plurality of physical stick-like hands forming analog indicators and at least a digital display area.

13. The device according to claim 1 wherein the electronic board comprises a hole, the size of the hole being adapted for inserting the air quality sensor through the hole, the sensor emerging from both sides of the electronic board.

14. The device according to claim 1, wherein the display arrangement further comprises a multi-color indicator LED, whose color is controlled by the electronic board according to a sensed level of air pollutants in the sampled air.

15. The device according to claim 1, further comprising a vibrator, controlled by the electronic board which is configured to activate the vibrator if a sensed level of pollutants exceeds a predefined threshold.

16. The device according to claim 1, wherein the cavity is elsewhere isolated from the inside of the housing by using at least one gasket.

17. The device according to claim 1 wherein the internal area of the cavity is in fluid communication with the ambient air exclusively through the membrane, the cavity being elsewhere isolated from the inside of the housing.

* * * * *